US00PP30263P3

(12) United States Plant Patent
Plocher

(10) Patent No.: US PP30,263 P3
(45) Date of Patent: Mar. 5, 2019

(54) GRAPE PLANT NAMED 'CRIMSON PEARL'

(50) Latin Name: ***Vitis* interspecific hybrid**
Varietal Denomination: Crimson Pearl

(71) Applicant: Thomas Alan Plocher, Hugo, MN (US)

(72) Inventor: Thomas Alan Plocher, Hugo, MN (US)

( * ) Notice: Subject to any disclaimer, the term of this patent is extended or adjusted under 35 U.S.C. 154(b) by 0 days.

(21) Appl. No.: 15/530,160

(22) Filed: Dec. 6, 2016

(65) Prior Publication Data

US 2018/0160590 P1 Jun. 7, 2018

(51) Int. Cl.
*A01H 5/08* (2018.01)
*A01H 6/88* (2018.01)

(52) U.S. Cl.
USPC ..... Plt./205
CPC ..... *A01H 5/08* (2013.01); *A01H 6/88* (2018.05)

(58) Field of Classification Search
USPC ..... Plt./205
CPC ..... A01H 5/0812
See application file for complete search history.

(56) References Cited

PUBLICATIONS https://www.winesandvines.com/news/article/158849/New-Cold-Climate-Grapes-Named; Oct. 6, 2015; 8 pages.*

* cited by examiner

*Primary Examiner* — Kent L Bell
(74) *Attorney, Agent, or Firm* — Michelle Bos Legal LLC

(57) ABSTRACT

'Crimson Pearl' is a late-budding grape variety notable for its winter hardiness, late bud break in springtime, and suitability as a red wine grape.

8 Drawing Sheets

Latin name: *Vitis* interspecific hybrid.
Variety denomination: 'Crimson Pearl'.

BACKGROUND OF THE VARIETY

'Crimson Pearl' is a new and distinct variety of grape plant selected from a group of seedlings resulting from a controlled cross of female parent 'MN 1094' (not patented) and male parent 'E.S. 4-7-26' (not patented) carried out at Hugo, Minn. in 1996. 'Crimson Pearl' was selected for its excellent winter hardiness, late bud break in springtime and excellent suitability as a red wine grape. Asexual propagation by hardwood cutting was first carried out in 2002 at Hugo, Minn.; subsequent asexual propagations have shown the variety to be stable and to reproduce true to type through successive generations.

BRIEF DESCRIPTION OF THE VARIETY

'Crimson Pearl' is a late-budding grape variety notable for its winter hardiness, late bud break in springtime, and suitability as a red wine grape.

A comparison of 'Crimson Pearl' to its parents is shown in Table 1 below.

TABLE 1

Comparison of 'Crimson Pearl' to Parent Varieties

| | 'Crimson Pearl' | 'MN 1094' | 'ES 4-7-26' |
|---|---|---|---|
| Winter hardiness | Primary bud hardiness to −32 C. or colder | Primary bud hardiness to −40 C. | Primary bud hardiness to −30 C. |

TABLE 1-continued

Comparison of 'Crimson Pearl' to Parent Varieties

| | 'Crimson Pearl' | 'MN 1094' | 'ES 4-7-26' |
|---|---|---|---|
| Bud break | Later | Earlier | Earlier |
| Acidity at harvest | 0.8% | 1.2% | 1% |
| pH | 3.40 | 3.20 | 3.25 |
| Berry size | 14.78 mm avg. diameter | 6 mm | 14 mm |
| Cluster size | 110 g | 45 g | 140 g |

A comparison of 'Crimson Pearl' to 'Marquette' (U.S. Plant Pat. No. 19,579), another cold-hardy variety, is shown in Table 2 below.

TABLE 2

Comparison of Crimson Pearl to Similar Variety

| | 'Crimson Pearl' | 'Marquette' |
|---|---|---|
| Winter hardiness | Very hardy | Hardy |
| Bud break | Late April, about 12 days after 'Marquette' | Mid-April |
| Acidity at harvest | Lower - 0.8% | Higher - 1.1% to 1.2% |
| Vigor | Less vigorous; fewer lateral shoots | More vigorous; more lateral shoots |
| Skin tannins | Higher concentration, extractible | Lower concentration, not extractible (protein bound) |

BRIEF DESCRIPTION OF THE PHOTOGRAPHS

The photographs show selected characteristics of a ten-year-old 'Crimson Pearl' grape plant grown on its own roots, taken during the 2016 growing season at Hugo, Minn.

Figure 1:
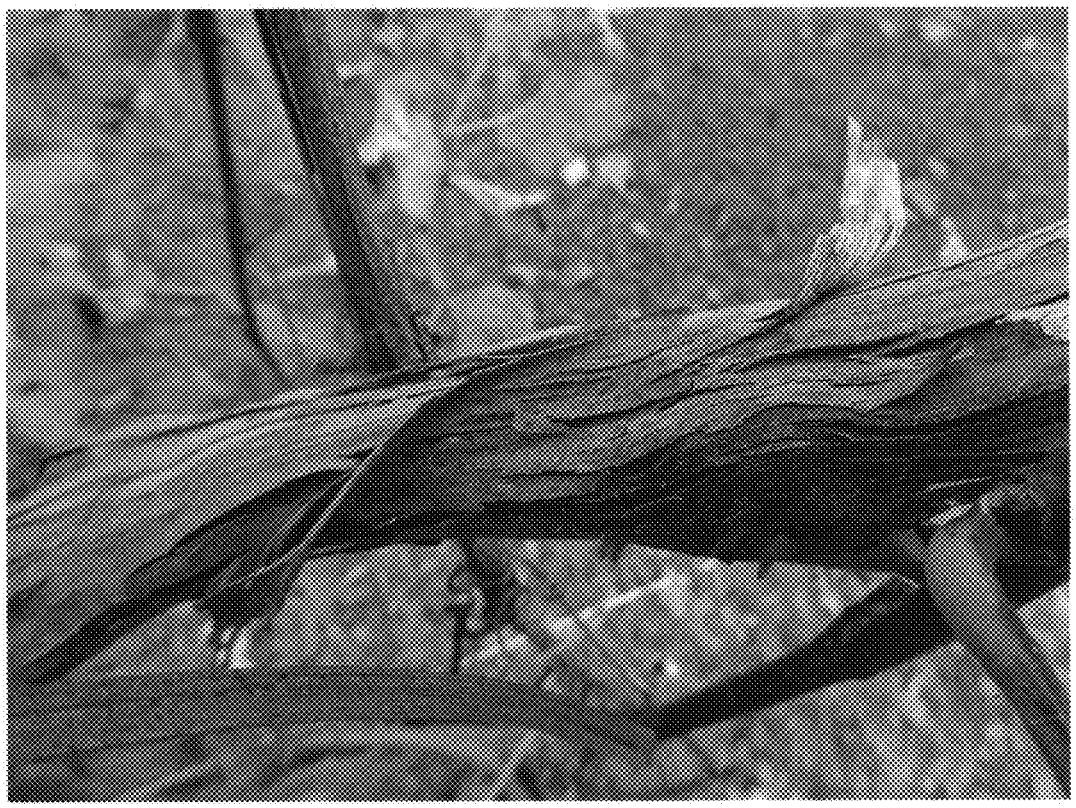
Figure 2:
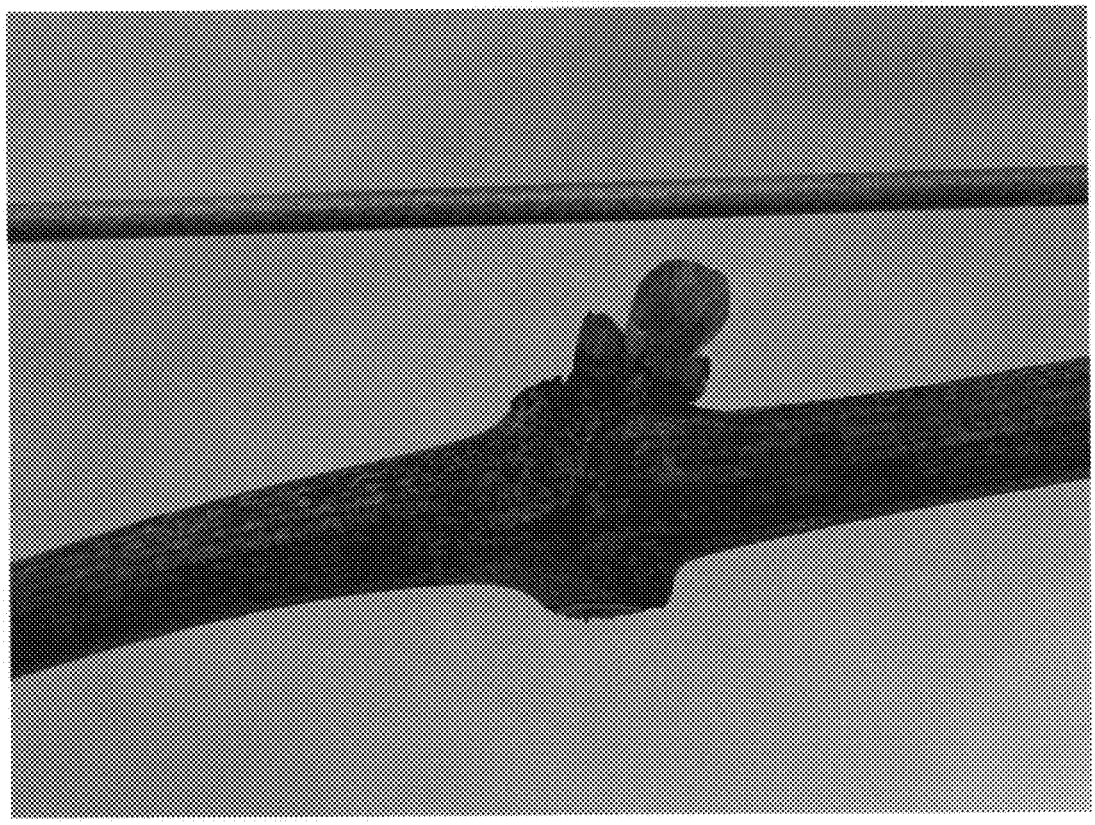
Figure 3:
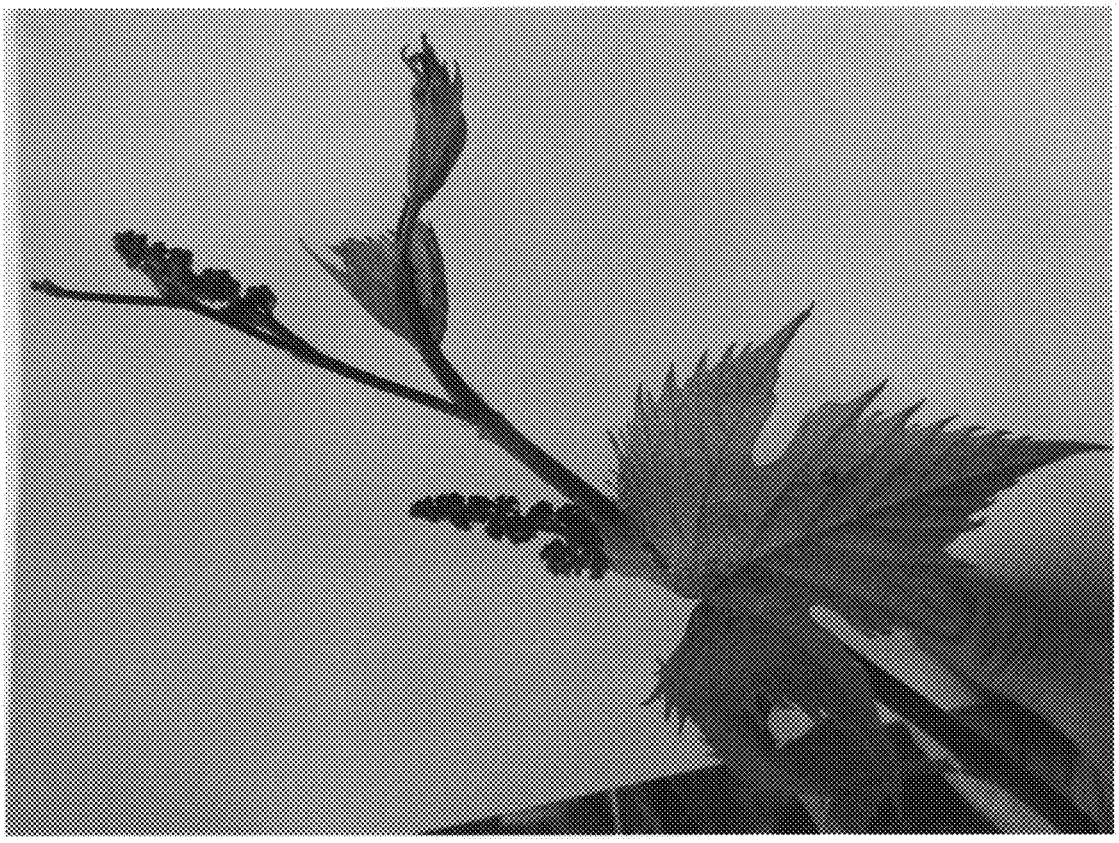
Figure 4:
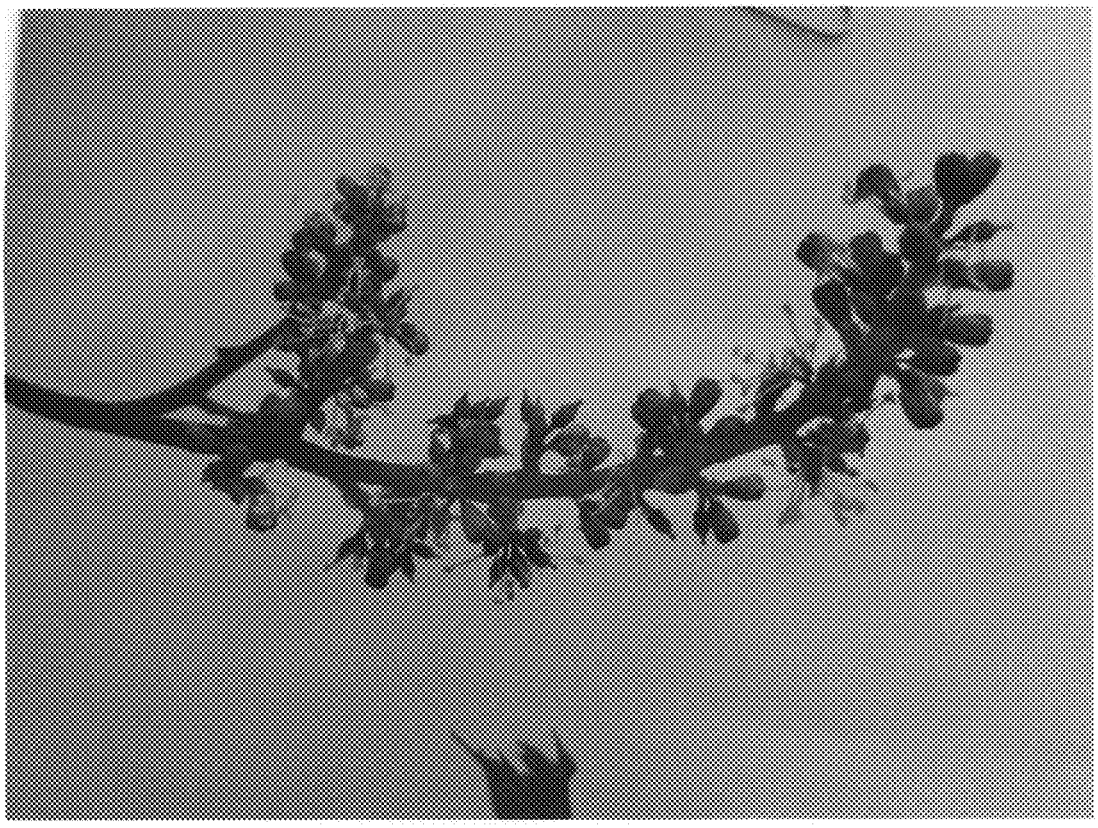
Figure 5:
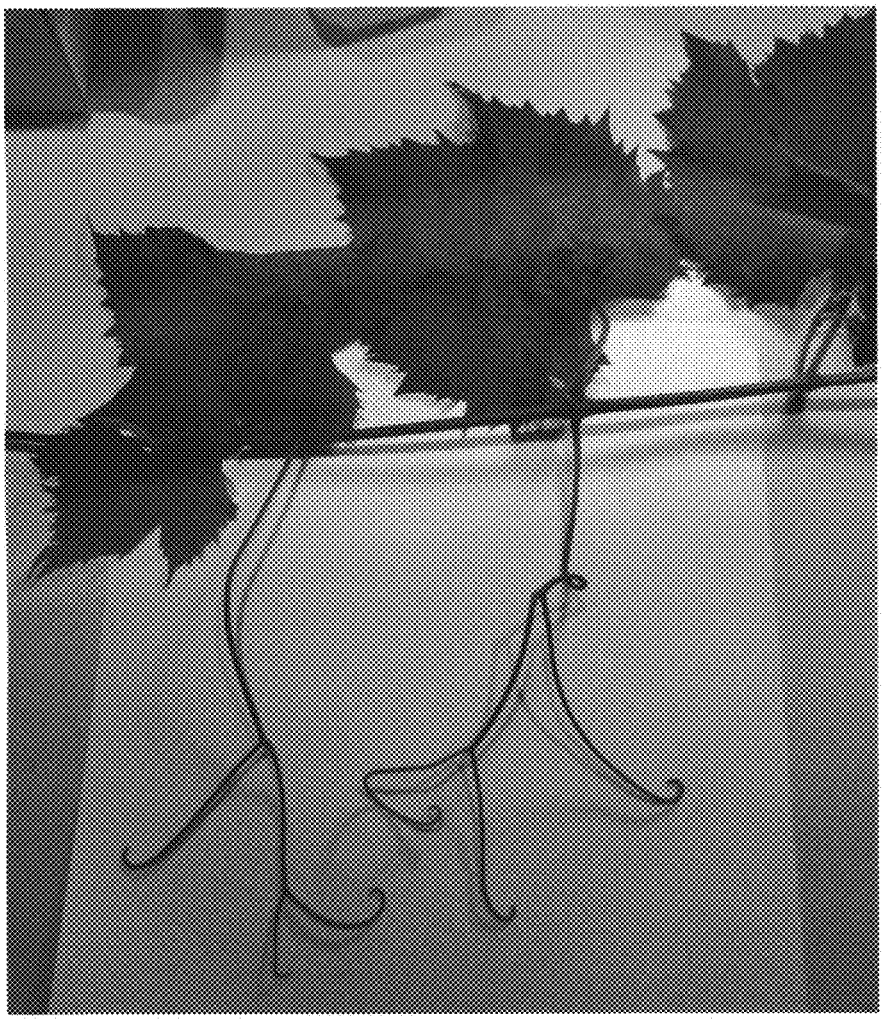
Figure 6:
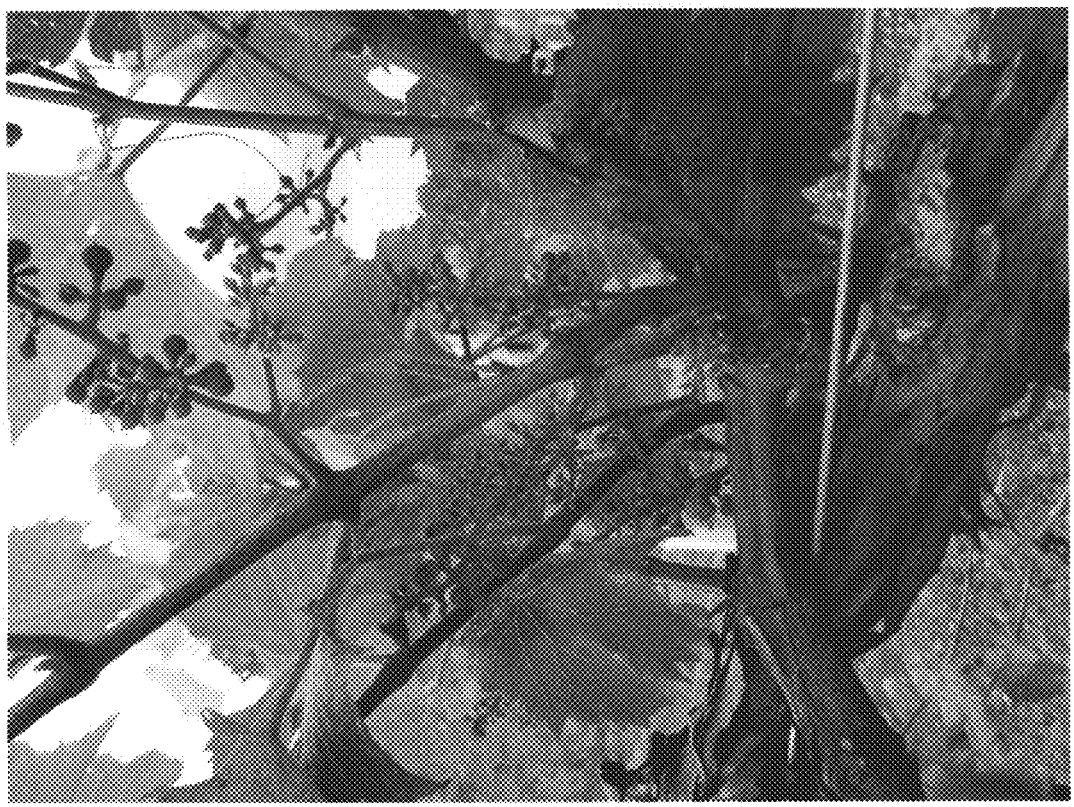
Figure 7:
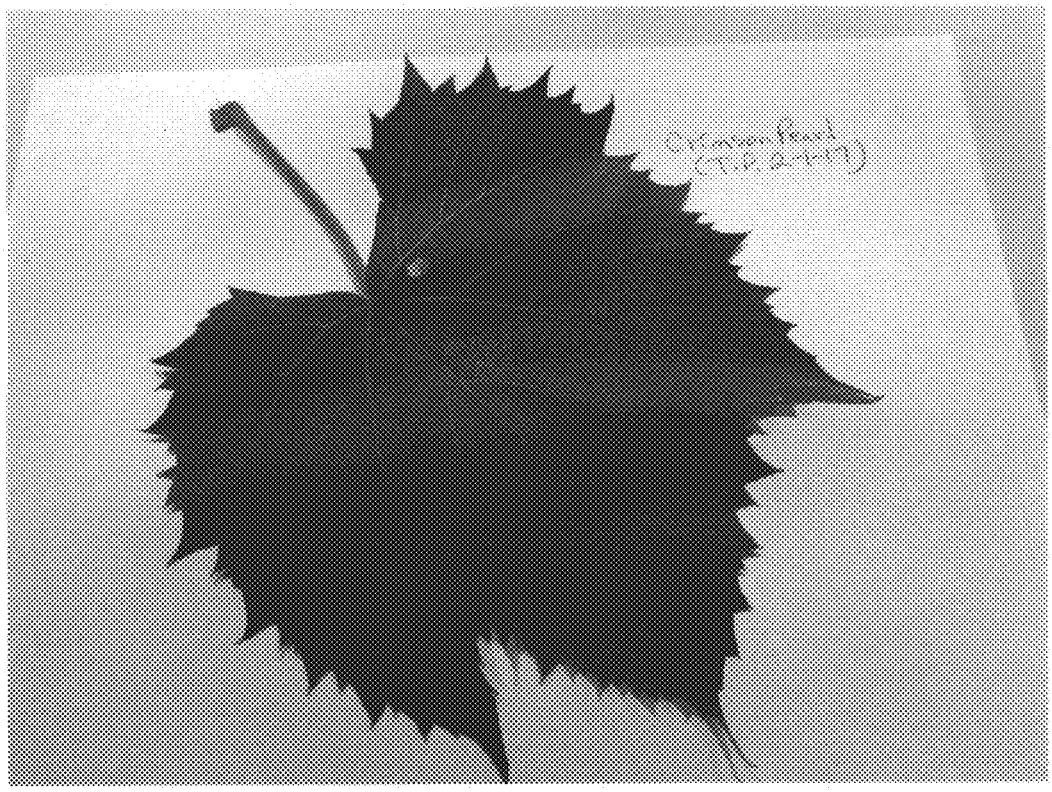
Figure 8:
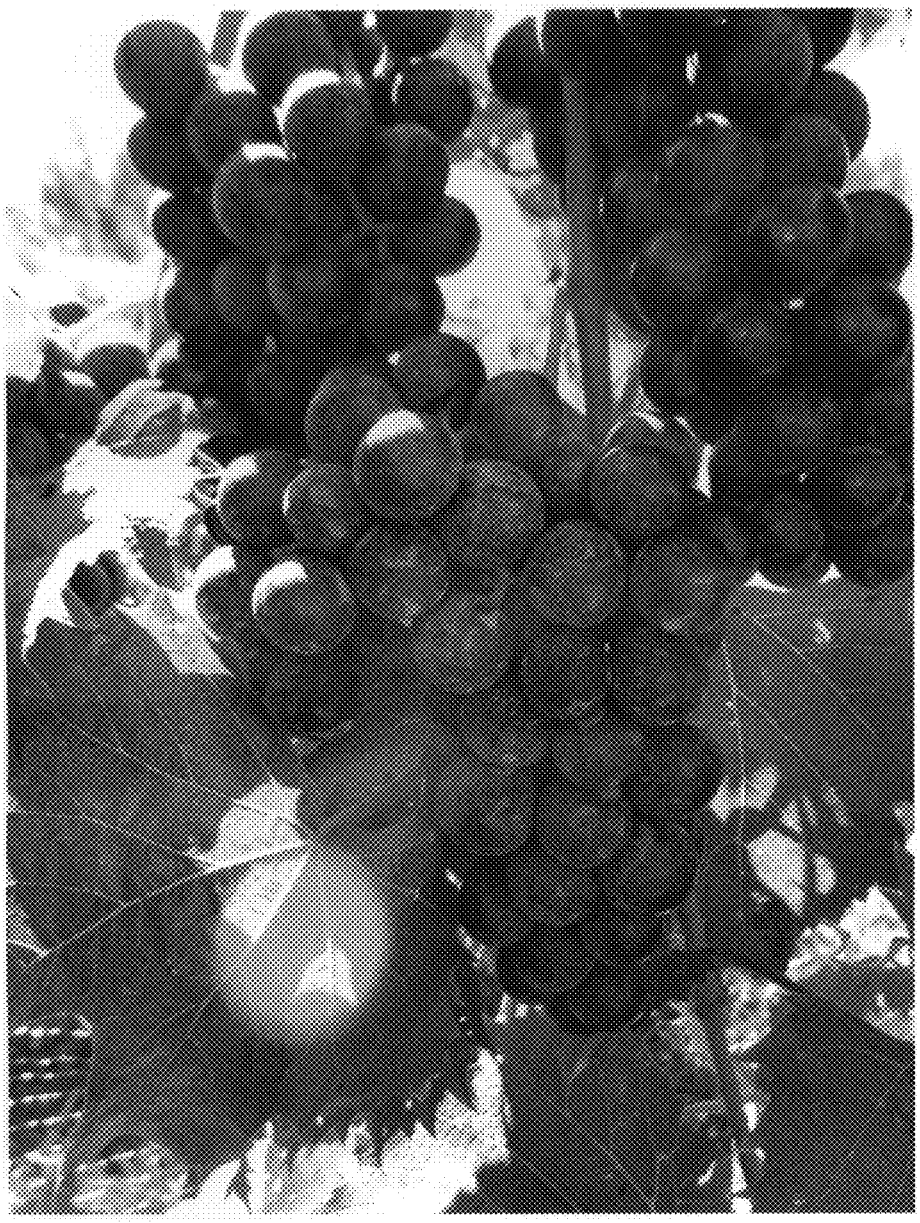

FIG. 1 shows the vine and bark;
FIG. 2 shows a bud at first swell stage;
FIG. 3 shows a young shoot and leaves;
FIG. 4 shows an inflorescence;
FIG. 5 shows leaves and tendrils;
FIG. 6 shows the vine, leaves, young shoots and inflorescences;
FIG. 7 shows a leaf; and
FIG. 8 shows a typical cluster and leaf.

DETAILED BOTANICAL DESCRIPTION OF THE VARIETY

The following-detailed botanical description is based on observations made during the 2016 growing season at Hugo, Minn. of ten-year-old vines growing on their own roots. All colors are described according to The Royal Horticultural Society Colour Chart (Sixth edition). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. "DDF 50" means "Degree Days Fahrenheit Base 50" and refers to accumulated heat units.

Vine:
- *Size*.—Vines are medium-sized owing to their moderate vigor.
- *Form*.—Procumbent.
- *Vigor*.—Moderate.
- *Timing of bud burst*.—30 Apr. 2016 (100% first swell stage at 112 DDF 50); approximately 12 days later than 'Marquette'.
- *Productivity*.—3 to 4 tons per acre on average soil.
- *Trunk diameter*.—3.5 cm at 76 cm above the ground.
- *Bark texture*.—Exfoliating.
- *Bark color*.—Brown N200B.

Canes:
- *Diameter*.—7 mm (measured immediately distal to $4^{th}$ node).
- *Quantity*.—Typical pruning to 30 buds giving rise to 30 canes.
- *Bark color*.—Greyed-orange 175A.
- *Bark texture*.—Smooth with moderate longitudinal lines.
- *Form*.—Slightly flattened in cross section.
- *Node size*.—13 mm (measured at $4^{th}$ node).
- *Internode length*.—8 cm (measured between $3^{rd}$ and $4^{th}$ full node).
- *Number of tendrils per node*.—Pattern is two consecutive nodes, each with a single tendril, followed by one or two consecutive nodes with no tendrils.
- *Tendril color*.—Dark Red 59A, going to Strong Yellow Green 144B at the tips.
- *Tendril thickness*.—1.2 to 2.0 mm, average 1.6 mm.
- *Tendril length*.—Natural (uncurled) 14.7 cm; stretched 15.7 cm.
- *Tendril texture*.—Smooth.

Flowers:
- *Fertility*.—Self-fertile.
- *Date of bloom*.—11 Jun. 2016 (approximately 465 DDF 50 from 100% first swell to 50% caps off).
- *Number of inflorescences per shoot*.—3.
- *Numbers of flowers per inflorescence*.—200.
- *Shape of flower cluster*.—Cylindrical with a small wing; Proximal half of cluster is straight, distal half is curved to subtend an angle of about 30 degrees.
- *Length of flower cluster*.—11 cm.
- *Width of flower cluster*.—Ranges from 2 cm for the main cluster to 3.6 at the widest point of the wing.
- *Pedicel length*.—2 mm.
- *Pedicel diameter*.—0.15 mm.
- *Pedicel color*.—Green 142A with orange-red N34A to orange-red N34B where pedicel meets pistil.
- *Filament length*.—4 mm.
- *Filament color*.—White N155D.
- *Anther length*.—1 mm.
- *Anther color*.—Yellow 11B.
- *Pistil length*.—2.0 to 2.25 mm.
- *Pistil diameter*.—0.8 mm.
- *Pistil color*.—Green 142A; some pistils show orange-red N34A to orange-red N34B around the stigma.
- *Flower stem color*.—Green 142A with orange-red N34A to orange-red N34B where stem meets pistil.
- *Flower type*.—Hermaphroditic.
- *Stamen color*.—White N155D.
- *Stamen length*.—4 mm.
- *Stamen quantity*.—4 to 6.
- *Cap color*.—Green 142A with a splash of orange-red N34A to orange-red N34B in the center of the cap.

Young shoots (measured at flowering):
- *Openness of the tip*.—Slightly open.
- *Density of prostrate hairs on tip*.—Medium density, predominantly follow underside of veins.
- *Anthocyanin coloration of prostrate hairs on tip*.—Hairs on the veins lack coloration; hairs between veins are red-purple 64B.

Young leaf ($4^{th}$ distal leaf at flowering):
- *Shape*.—Circular.
- *Length*.—11.2 cm to 17 cm, average 13.7 cm.
- *Width*.—11 cm to 14.5 cm, average 12.2 cm.
- *Color of upper side of the blade*.—Green 143A.
- *Color of lower side of the blade*.—Strong Yellow Green 144A with occasional Dark Red 59A coloration of the veins at their branching points.
- *Density of prostrate hairs between main veins on lower side of blade*.—Present but sparse.
- *Density of erect hairs on main veins on lower side of blade*.—Strong, especially along both sides of the vein, but also quite strong on top of the vein.

Mature leaves (measured just before veraison):
- *Relative size*.—Medium.
- *Length*.—14.5 to 19.0 cm, average 16.4 cm.
- *Width*.—14.5 to 20.0 cm, average 17.2 cm.
- *Thickness*.—0.015 mm to 0.017 mm, average 0.016 mm.
- *Shape*.—Circular.
- *Base*.—Cordate.
- *Margin*.—Erose.
- *Color*.—Upper surface — Green group 139, in between 139A and 139B (dark yellowish green and moderate yellowish green).
- *Color*.—Lower surface — Yellow-green 144A.
- *Texture*.—Upper surface — Hairless between veins and moderately corrugated; some short semi-prostrate hairs on veins.

*Texture.*—Lower surface — Hairless between veins and moderately corrugated; moderate erect hairs on the veins.
*Number of lobes.*—3.
*Terminal lobe.*—Form — Pointed.
*Petiole color.*—Red-purple 59C, with yellow-green 143B striping; striping is wider and more pronounced at distal half of petiole.
*Petiole sinus depth.*—1.5 to 4.0 cm, average 2.83 cm.
*Petiolar sinus shape.*—V-shaped.
*Petiolar sinus.*—Relative arrangement of lobes — Very wide open.
*Petiole sinus limited by veins?.*—Yes.
*Anthocyanin coloration of main veins on upper side of blade.*—Deep Red 60A until first bifurcation.
*Petiole length.*—5.5 to 9.6 cm, average 7.96 cm.
*Petiole diameter.*—3.0 mm to 4.4 mm, average 3.6 mm.
*Density of prostrate hairs between main veins on lower side of blade.*—Sparse.
*Density of erect hairs on main veins on lower side of blade.*—Medium.
*Length of middle vein.*—12.0 to 14.3 cm, average 13.1 cm.
*Petiole length/length of middle vein.*—0.46 to 0.74, average 0.61.
*Lateral sinus depth.*—Left side — 1.7 to 4.7 cm, average 2.84 cm.
*Lateral sinus depth.*—Right side — 1.5 to 4.7 cm, average 2.83 cm.
*Lateral sinus shape.*—Shallow U-shape or V-shape; often asymmetrical.
*Relative arrangement of lateral sinus lobes.*—Open.
*Margin.*—Teeth shape (noted between N2 and N3) — Mostly rectilinear; a few convex on both sides, and a few convex on one side and concave on the other side.
*Length of teeth.*—0.8 to 1.6 cm, average 1.17 cm.
*Width of teeth.*—0.6 to 1.4 cm, average 1.03 cm.
*Ratio of length/width of teeth.*—0.67 to 1.1, average 0.9.

Mature tendrils (measured after veraison, August 27):
*Quantity.*—Pattern is two consecutive nodes, each with a single tendril, followed by one or two consecutive nodes with no tendrils.
*Thickness.*—1.1 to 2.0 mm, average 1.55 mm.
*Length.*—Natural (uncurled) 14.7 cm; stretched 15.67 cm.
*Tendril color.*—Deep Red 60A with Strong Yellow Green N144D on tips.
*Texture.*—Smooth.

Shoot (measured at flowering):
*Attitude (before tying).*—45-60 degrees measured at the base of the shoot between the shoot and the cane from which it grew.
*Color of dorsal side of internode (well illuminated).*—Orange-red N34D overlaid with red-purple 59A speckle and striping.
*Color of ventral side of internode (without direct sunlight).*—Yellow-green 143B.
*Density of erect hairs on internodes.*—Medium.
*Length of tendrils.*—18 to 22 cm, stretched out.
*Thickness of tendril.*—1.25 mm (measured just proximal to the branching).
*Form of tendril.*—With two points of branching, one halfway up the tendril and the other at the end of one of the first branches.
*Texture of tendril.*—Ribbed with erect hairs present, but sparse.
*Number of consecutive tendrils.*—Discontinuous; pattern is 2 consecutive nodes with tendrils followed by 1 or 2 nodes with no tendril.
*Color of tendril.*—Dominant appearance from top of tendril is red-purple 59A with some Strong Yellow Green 144A here and there on the underside of the tendril.

Fruit:
*Maturity date.*—155 days after bud break, or 2548 DDF 50, in Hugo, Minn. (45.1600° N, 92.9933° W); Relative timing is mid-season, mid-to late September.
*Shape.*—Round and slightly flattened (width slightly exceeds length).
*Length.*—13.37 to 15.7 mm, average 14.39 mm.
*Width.*—13.82 to 15.8 mm, average 14.78 mm.
*Relative size.*—Larger than 'Petite Pearl' (not patented); smaller than 'Verona' (U.S. Plant patent application Ser. No. 15/530,152).
*Brix.*—22 degrees.
*Skin thickness.*—0.47 to 0.58 mm, average 0.52 mm.
*Skin color.*—Blue 103A overlaid with some violet-blue 98A.
*Tendency to crack.*—No tendency to crack, even under wet conditions.
*Flesh color.*—Greenish White N155C to Pale Yellow Green 157B with some Deep Red 60A anthocyanin streaks.
*Flesh texture.*—Slipskin; gelatinous.
*Juice color.*—Strong Purplish Red 64C.
*Juice production.*—16 lbs. (7.26 kg) fruit produces 1 gallon (3.78 L) finished wine.
*Anthocyanin coloration.*—Some Deep Red 60A coloration around seeds inside pulp.
*Flavor.*—Fruity, no labrusca flavor.
*Aroma.*—Sweet, fruity.
*Seed length.*—Average 6.8 mm.
*Seed width.*—Average 3.9 mm.
*Seed thickness.*—2.99 mm.
*Seed shape.*—Pyriform.
*Seed color.*—Grey-brown N199C to N199D.

Cluster:
*Overall shape.*—Cylindrical with a wing often borne on a long pedicel; slightly loose to compact.
*Relative size.*—Larger than 'Petite Pearl'; smaller than 'Verona'.
*Weight.*—70 to 149 g, average 110 g.
*Number of berries per cluster.*—47 to 83, average 62.6 berries per cluster.
*Length.*—8.0 to 14.5 cm, average 11.2 cm.
*Width.*—4.5 to 8.5, average 7.3 cm.
*Peduncle length.*—4.67 to 6.98 mm, average 5.618 mm.
*Peduncle thickness.*—1.22 to 2.10 mm, average 1.711 mm.
*Peduncle color.*—Strong Yellow Green 143B overlaid with Dark Red 59A.
*Pedicel length.*—21 to 33 mm, average 27.69 mm.
*Pedicel thickness.*—2.38 to 3.39 mm, average 2.82 mm.

Market use: Production of red wine.

Disease resistance/susceptibility: High resistance to downy mildew (*Plasmopara viticola*) and powdery mildew (*Erysiphe necator* (Schw.) Burr.); Good resistance to black rot (*Guignardia bidwellii*); Some susceptibility to *Phomopsis* (*Phomopsis viticola*) reported in New England.

I claim:

1. A new and distinct grape plant substantially as described and illustrated herein.

* * * * *